United States Patent [19]

Morris

[11] 4,316,990

[45] Feb. 23, 1982

[54] PREPARATION OF α,β-ALDEHYDES BY ALDOL CONDENSATION

[75] Inventor: Don L. Morris, Longview, Tex.

[73] Assignee: Eastman Kodak Company, Rochester, N.Y.

[21] Appl. No.: 201,954

[22] Filed: Oct. 29, 1980

[51] Int. Cl.$^3$ .................... C07C 45/72; C07C 47/20
[52] U.S. Cl. ................................ 568/461; 568/459; 568/463
[58] Field of Search ............... 568/461, 458, 463, 459

[56] References Cited

U.S. PATENT DOCUMENTS

| | | | |
|---|---|---|---|
| 1,896,240 | 2/1933 | Jaeger | 568/461 |
| 3,542,878 | 11/1970 | Swift | 568/461 |
| 3,948,991 | 4/1976 | Chan et al. | 568/461 |

FOREIGN PATENT DOCUMENTS

| | | | |
|---|---|---|---|
| 2505580 | 9/1975 | Fed. Rep. of Germany | 568/459 |
| 45675 | 4/1962 | Poland | 568/461 |

*Primary Examiner*—Werren B. Lone
*Attorney, Agent, or Firm*—Clyde L. Tootle; Daniel B. Reece, III

[57] ABSTRACT

In the present invention aliphatic aldehydes are condensed to form α,β-unsaturated aldehydes by use of a heterogeneous catalyst. Such process uses an anatase titanium dioxide catalyst in a fixed bed process under mild temperature conditions to yield high conversions and high yields, and which also eliminates the catalyst removal steps required by conventional processes.

15 Claims, No Drawings

PREPARATION OF α,β-ALDEHYDES BY ALDOL CONDENSATION

This invention relates to condensing aliphatic aldehydes to form α,β-unsaturated aldehydes by use of a heterogeneous catalyst. For example, a catalyst such as anatase titanium dioxide can be used in a fixed bed process. The use of such a process eliminates the catalyst removal steps required by conventional processes.

It is well known in the art to use homogeneous for the condensation of aldehydes to provide α,β-unsaturated aldehyde. Such aldol catalysts as noted in the literature include, for example, the conventional sodium, potassium, magnesium or calcium hydroxide catalyzed aldol processes. These processes provide good conversions and yields but also require removal of the catalyst, sometimes requiring more than one step catalyst removal processes. Other heterogeneous catalyst are known in the art which do not require the necessary catalyst removal. For example, Swift, Bozik and Massoth [U.S. Pat. No. 3,542,878 (1970)] and Chun and Massoth [U.S. Pat. No. 3,948,991 (1972)] describe the use of metalic tin supported on silica gel as a catalyst for the condensation of n-butyraldehyde to 2-ethylhexanal in a vapor phase reaction. Hydrogen must be fed to maintain catalyst activity. The use of $Al_2O_3$ or sodium oxide and potassium oxide supported on alumina is described in German Pat. No. 2,505,580 (1976) for the condensation of aldehydes and ketones. Numerous patents for the preparation of mesityl oxide from acetone or acrolein from acetaldehyde have been issued based on the use of silica gel, alumina or zeolites as catalysts. However, the above heterogeneous catalysts are generally employed as vapor phase catalysts at temperatures of from 200° to 400° C. in order to attain commercially significant activity and selectivity for synthesis of α,β-unsaturated carbonyl compounds. Operating at these high temperatures reduces the life of the catalyst and provides a more expensive process. Therefore, it would be an unexpected advance in the state of the art to provide a process for the preparation of α,β-unsaturated aldehydes by aldol condensation operated under mild temperature conditions, which has long catalyst life, and eliminates catalyst removal operations.

In accordance with the present invention, an aldol condensation process is provided for preparing α,β-unsaturated aldehydes from aliphatic aldehydes by the use of an anatase titanium oxide catalyst operated at a temperature of about 100° C. to about 300° C. The process of the present invention is advantageous over previously reported processes in that it provides very high selectivity for the formation of the desired condensation products and long catalyst life. In addition to selectivity, the process provides a high activity which enables the use of the catalyst at relatively mild temperatures to provide high production rates of the condensation products. The anatase titanium dioxide catalyst can preferably be prepared by the hydrolysis of titanium tetrachloride with ammonium hydroxide or by digestion of anatase titanium dioxide with a metal hydroxide, such as sodium hydroxide, followed by reprecipitation with an acid. Such catalyst syntheses are described by H. Hattori, M. Itol and K. Tanabe in J. Catalysis 38, 172 (1975) and are acceptable; however, commercial titanium dioxide supplied by Harshaw Chemical Company (Ti-0404) was found to be a very good catalyst.

The reaction is best carried out in the liquid phase, that is, under enough pressure to maintain all the reactants in the liquid phase and to transport the liquid through the reactor. Pressure of 200 psi has been found desirable, and can be maintained by the use of nitrogen which provides an inert blanket to exclude oxygen and air while providing a sweeping gas to force aldehyde through the column. Solid aldehydes can be used but they should first be dissolved in a suitable solvent such as ethanol or hexane. The reaction is carried out at temperatures of 100° C. to 300° C., preferably 125° C. to 180° C., most preferred 150° C. to 160° C. At temperatures lower than 100° C. the process is too slow to be commercially feasible. At temperatures greater than 300° C., the yield loss due to decomposition is excessive. The catalyst can conveniently be employed, for example, as a fixed bed or fluid bed and the aldehyde is passed over the catalyst at the desired temperature and pressure. The products are collected and recovered in a conventional fashion. In this manner, long catalyst life can be maintained with no catalyst recovery steps required during the product purification. Suitable aldehydes include saturated aliphatic aldehydes containing 2 to 8 carbon atoms, preferably 2 to 4 carbon atoms; such aldehydes include acetaldehyde, propionaldehyde, normal butyraldehyde. Depending on the products desired the aldehydes can be reacted alone or as mixtures of such aldehydes. The rate of reaction depends on feed rates of the aldehyde to amount catalyst. A feed of two volumes liquid to one volume catalyst is preferred. Greater volumes fed through provide less conversion.

This invention will be further illustrated by the following examples although it will be understood that these examples are included merely for purposes of illustration and are not intended to limit the scope of the invention.

EXAMPLE 1

100 Milliliters anatase titanium dioxide (Harshaw Ti-0404 as ⅛-inch pellet) was placed in a 0.75 inch by 36 inch stainless steel tube and covered with eight inches of glass beads. The tube was constructed to allow nitrogen and n-butyraldehyde to be fed to the top under pressures up to 500 psig. The liquid products were collected in a steel tank at the base. The gaseous products vented through a control valve to a dry ice trap. The tube was heated by electrical resistance tape with a thermoelectric controller and monitored through a concentric thermowell. The n-butyraldehyde was fed to the tube at 100 milliliters per hour and the temperature was maintained at 150° C. The nitrogen pressure was 280 psig with a purge of 160 milliliters per minute maintained through the control valve. The liquid products were analyzed by gas chromotography and distillation. The aldehyde conversion was 80 percent and the enal yield was 94 mole percent.

EXAMPLE 2

Example 1 was repeated except that the temperature was maintained at 153° C. and the feed rate increased to twice that of Example 1. The aldol conversion dropped to 58 percent and the mole enal yield was still 94 percent. This example shows that doubling the feed rate decreases the aldehyde conversion but does not decrease the yield.

EXAMPLE 3

Example 1 was repeated except that the rutile form of titanium dioxide was substituted for the anatase form of titanium dioxide and the temperature maintained at 170° C. The aldehyde conversion was 28 percent and the enal yield was 60 mole percent.

EXAMPLE 4

Example 1 was repeated except that silicon dioxide was substituted for the anatase form of titanium dioxide. The aldehyde conversion was 15 percent and the enal yield was 85 mole percent.

EXAMPLE 5

Example 1 was repeated except that zinc oxide was substituted for the anatase form of titanium dioxide and the temperature was maintained at 165° C. The aldehyde conversion was 32 percent and the enal yield was 41 mole percent.

EXAMPLE 6

Example 1 was repeated except that thorium dioxide was substituted for anatase titanium dioxide and the temperature maintained at 182° C. The aldehyde conversion was 5 percent and the enal yield was 64 mole percent.

EXAMPLE 7

Example 1 was repeated except that magnesium oxide was substituted for the anatase titanium dioxide and the temperature maintained at 160° C. The aldehyde conversion was 57 percent and the enal yield was 64 mole percent.

EXAMPLE 8

Example 1 was repeated except that propionaldehyde was substituted for n-butyraldehyde. The aldehyde conversion was 65 percent and the 2-methyl-2-pentenal yield was 88 mole percent.

EXAMPLE 9

Example 4 was repeated except that propionaldehyde was substituted for n-butyraldehyde. The aldehyde conversion was 7 percent and the 2-methyl-2-pentenal yield was 85 mole percent.

EXAMPLE 10

Example 9 was repeated except that the temperature was maintained at 200° C. The aldehyde conversion was 76 percent and the enal yield was 62 mole percent.

EXAMPLE 11

Example 1 was repeated except that aluminum oxide was substituted for the anatase form of titanium dioxide and propionaldehyde was substituted for n-butyraldehyde and the temperature maintained at 157° C. The aldehyde conversion was 22 percent and the enal yield was 68 mole percent.

EXAMPLE 12

Example 11 was repeated except that magnesium oxide was substituted for aluminum oxide and the temperature maintained at 160° C. instead of 157° C. The aldehyde conversion was 57 percent and the enal yield was 54 mole percent.

Yield is most significant because the yield is the amount of product formed in passing the aldehyde through the reactor over the catalyst divided by the aldehyde consumed. The conversion is the percent of aldehyde consumed per pass through the reactor. The process of the present invention shows in Example 1 that 80% of the aldehyde passing through the reactor is consumed and there is 94 percent yield of product formed per pass through the reactor. Example 2 shows that by decreasing the residence time on the catalyst by one-half that of Example 1, the conversion was reduced to 58 percent but the yield still remained at 94%. Example 3 shows that using a different crystalline form of titanium dioxide provides lower yields and conversions. Examples 5 to 7 shows that other metal oxides which are conventional aldol conversion catalyst likewise provide substantially lower yields and conversions. Example 8 shows that the process of the present invention using propionaldehyde shows lower conversion and lower yields than that obtained in converting butyraldehyde to 2-ethylhexenal. However, the present invention provides higher conversion and higher yields when converting propionaldehyde to 2-methylpentenal than other conventional oxide catalysts as shown by Examples 9, 11 and 12. Example 10 shows an increase in conversion by increase in temperature resulting in a lowering of yield. Therefore, it is apparent that the present invention provides a high yield, synthetic method that is commercially important because of the simplicity and availability of the catalyst, the ease of isolation of the products, and the mild condition required for high conversions of the aldehyde to $\alpha,\beta$-unsaturated aldehydes.

The invention has been described in detail with particular reference to preferred embodiments thereof, but it will be understood that variations and modifications can be effected within the spirit and scope of the invention.

I claim:

1. An aldol condensation process for preparing $\alpha,\beta$-unsaturated aliphatic aldehydes comprising passing an aliphatic saturated aldehyde containing 2 to 8 carbon atoms at a temperature of about 100° C. to about 300° C. over an anatase form titanium dioxide catalyst.

2. An aldol process according to claim 1 wherein said aliphatic saturated aldehyde is passed over said catalyst at a feed rate of two volumes aliphatic saturated aldehyde to one volume catalyst.

3. An aldol process according to claim 2 wherein said process is carried out under a pressure of at least 200 psi maintained by the use of nitrogen.

4. An aldol process according to claim 3 wherein said aliphatic saturated aldehyde is n-butyraldehyde.

5. An aldol process according to claim 3 wherein said aliphatic saturated aldehyde is propionaldehyde.

6. An aldol condensation process for preparing $\alpha,\beta$-unsaturated aliphatic aldehydes comprising passing an aliphatic saturated aldehyde containing 2 to 8 carbon atoms at a temperature of about 125° C. to about 180° C. over an anatase form titanium dioxide catalyst.

7. An aldol process according to claim 6 wherein said aliphatic saturated aldehyde is passed over said catalyst at a feed rate of two volumes aliphatic saturated aldehyde to one volume catalyst.

8. An aldol process according to claim 7 wherein said process is carried out under a pressure of at least 200 psi maintained by the use of nitrogen.

9. An aldol process according to claim 8 wherein said aliphatic saturated aldehyde is n-butyraldehyde.

10. An aldol process according to claim 8 wherein said aliphatic saturated aldehyde is propionaldehyde.

11. An aldol condensation process for preparing $\alpha,\beta$-unsaturated aliphatic aldehydes comprising passing an aliphatic saturated aldehyde containing 2 to 8 carbon atoms at a temperature of about 150° C. to about 160° C. over an anatase form titanium dioxide catalyst.

12. An aldol process according to claim 11 wherein said aliphatic saturated aldehyde is passed over said catalyst at a feed rate of two volumes aliphatic saturated aldehyde to one volume catalyst.

13. An aldol process according to claim 12 wherein said process is carried out under a pressure of at least 200 psi maintained by the use of nitrogen.

14. An aldol process according to claim 13 wherein said aliphatic saturated aldehyde is n-butyraldehyde.

15. An aldol process according to claim 13 wherein said aliphatic saturated aldehyde is propionaldehyde.

* * * * *